United States Patent [19]

Milthorpe et al.

[11] Patent Number: 4,911,710

[45] Date of Patent: Mar. 27, 1990

[54] TREATMENT OF COLLAGENOUS TISSUE

[75] Inventors: Bruce Milthorpe, Naremburn; Klaus Schindhelm, Cherrybrook, both of Australia

[73] Assignee: Domedica Pty. Limited, New South Wales, Australia

[21] Appl. No.: 95,169

[22] PCT Filed: Nov. 13, 1986

[86] PCT No.: PCT/AU86/00346

§ 371 Date: Jul. 13, 1987

§ 102(e) Date: Jul. 13, 1987

[87] PCT Pub. No.: WO87/02880

PCT Pub. Date: May 21, 1987

[30] Foreign Application Priority Data

Nov. 13, 1985 [AU] Australia ............................ PH3384

[51] Int. Cl.$^4$ ............................................. A61F 2/02
[52] U.S. Cl. ........................................ 623/66; 623/11; 128/DIG. 8
[58] Field of Search ....................... 623/11, 66, 12, 13, 623/15, 1; 128/DIG. 8; 8/94.19 R; 530/356, 842; 424/95

[56] References Cited

U.S. PATENT DOCUMENTS

| | | |
|---|---|---|
| 3,189,401 | 6/1965 | Griset . |
| 3,523,027 | 8/1970 | Hall . |
| 3,557,078 | 1/1971 | Feairheller . |
| 3,560,141 | 2/1971 | Kurilla . |
| 3,930,036 | 12/1975 | Burke . |
| 4,082,507 | 4/1978 | Sawyer . |
| 4,120,649 | 10/1978 | Schechter . |
| 4,349,026 | 9/1982 | Miyata ........................... 128/DIG. 8 |
| 4,383,832 | 5/1983 | Fraefel . |
| 4,399,123 | 8/1983 | Oliver et al. ....................... 623/11 X |

FOREIGN PATENT DOCUMENTS

| | | |
|---|---|---|
| 8505775 | 9/1975 | Australia . |
| 8602542 | 9/1975 | Australia . |
| 686710 | 9/1979 | U.S.S.R. . |
| 1122505 | 4/1970 | United Kingdom . |

*Primary Examiner*—Alan W. Cannon
*Attorney, Agent, or Firm*—Oblon, Spivak, McClelland, Maier & Neustadt

[57] ABSTRACT

An implantable collagen-based material is prepared by (i) pretreating a collagen-based material with a member selected from the group consisting of fluorescein isothiocyanate, picrylsulphonic acid and nitrous acid, in an amount sufficient to render some of the amino acid side chains of the material unable to bind with a cross-linking agent, and (ii) reacting the pretreated collagen-based material with a cross-linking agent whereby at least some of the remaining amino acid side chains are linked together.

6 Claims, No Drawings

TREATMENT OF COLLAGENOUS TISSUE

TECHNICAL FIELD

This invention relates to the processing of collagenous tissues and collagenous based prostheses to provide materials suitable for human implantation.

BACKGROUND ART

The invention will be described in relation to Xenograft bioprostheses (ie: implant materials obtained from animals) for the replacement or repair of damaged human tendons and ligaments, but, it is to be understood that the invention is not limited thereto as the implantable materials of the invention may be used for other purposes such as patches for hernia repair and as intermediate-life sutures.

For some years, collagen-based animal or human tissues have been used as bioprostheses such as heart valves, blood vessels, ligaments and pericardium. These tissues have been treated with aldehydes such as glutaraldehyde to minimize their rejection potential (ie: antigenicity).

Australian Patent Specification 497,462 discloses a non-antigenic, non-thrombogenic, infection-resistant graft derived from the human umbilical cord. To provide such a graft, the Wharton's jelly (which surrounds the vein and the two arteries of the umbilical cord) is removed manually or by flushing with a saline solution. A mandrel is then inserted into the vein and the vein and the arteries are dissected our of the umbilical cord itself. The vein and arteries are then subjected to a tanning treatment with an aldehyde to stiffen the material. Glutaraldehyde is noted as being the preferred tanning agent from the stand points of elimination of any traces of antigenicity and thrombogenicity as well as convenience.

The vascular prostheses disclosed in Australian Patent Specification 516,741 consists of a coherent tubular wall of non-human collagenous tissue which has been subjected to glutaraldehyde tanning so as to provide cross-linked collagen fibres and a tubular reinforcement of fibre mesh embedded within the coherent wall of tanned collagenous tissue.

The tanning step is carried out in a bath of buffered glutaraldehyde and upon its completion all free glutaraldehyde is removed by washing in baths of saline and hydrogen peroxide. The buffered glutaraldehyde has a glutaraldehyde strength of 5% and the pH of the bath is held at about 7.4 by using sodium phosphate or potassium acid phosphate.

According to Australian Patent Specification 516,741 the desirable features of the ovine reinforced collagen conduit revolves around the glutaraldehyde treatment which alters the antigen combining sites to shield the Xenograft from immune reaction.

The vascular prostheses disclosed in Australian Patent Specification 64,816/80 is produced by subjecting a length of animal ureter to glutaraldehyde tanning. The ureter as discussed in the specification includes those from humans, oxen, cows, sheep, goats, pigs, donkeys, camels, deer and kangaroos. Tanning is carried out in a buffered glutaraldehyde bath having a glutaraldehyde strength of 2.5% by weight.

The modified bioprostheses disclosed in Australian Patent Specification 87,332/82 consists of a tissue specimen to which is bonded a mesh material so that the bioprostheses can be placed with at least a portion of the mesh against a living tissue surface to enable the living tissue to grow into the mesh. More specifically, that specification discloses the use of glutaraldehyde treated mammalian tendons but does not deal with the glutaraldehyde treatment itself.

Collagen is a protein which is the major fibrous component of skin, bone, tendon, cartilage, ligaments and blood vessels. Collagen is rich in glycine and also contains proline, hydroxyproline, lysine and hydroxylysine. As indicated above, glutaraldehyde is used to cross-link the amino acid side chains of the collagen, mainly lysine, to improve the strength of the collagen fibre, but, in so doing, much of its natural flexibility is lost and its ability to be resorbed by the body is also greatly reduced.

Thus, the aldehyde-fixed collagen which has improved mechanical strength and antigenicity does not lend itself to use as a Xenograft bioprostheses for the replacement or repair of damaged human tendons and ligaments because of its reduced flexibility and its inability to be resorbed. As a consequence, there is little replacement of the graft by host tissue with suitable properties.

At the present time, there is no satisfactory ligament or tendon substitute although many synthetic and biological materials have been tried. The most commonly used substitute is autogenous material (for example, patella tendon) but this is not always available or of adequate strength. There is, therefore, a need for a tendon or ligament substitute which possesses appropriate fineness, length, flexibility, strength and the ability to be replaced by endogenous tissue with desirable characteristics.

It is an object of this invention to provide human implantable collagen-based materials with desirable properties with respect to antigenicity and possessing mechanical strength and flexibility which will largely be replaced by endogenous tissue with suitable characteristics so as to be useable to repair or replace tendons and ligaments as well as for other purposes.

SUMMARY OF THE INVENTION

According to the invention there is provided a process for preparing a human implantable collagen-based material comprising the steps of:
  (i) pre-treating the collagen-based material so that some of the amino acid side chains of the material are rendered unable to bind with a crosslinking agent, and,
  (ii) reacting the pre-treated collagen-based material with a cross-linking agent whereby at least some of the remaining amino acid side chains are linked together.

Preferably, the collagen based material is pretreated with a reagent capable of reacting with or removing the primary amines of the amino acid side chains.

The process of the invention may be applied to the treatment of collagenous tissues in general and in particular to ligaments, tendons, heart valves, dura mater, pericardium, skin patches, blood vessels and ureters.

The collagen-based material may be selected from a wide range of animal sources such as bovine, porcine, ovine, equine and kangaroo.

Such treated tissues may be used as Xenografts for the replacement and repair of human tissues such as ligaments, tendons, heart valves, dura mater, pericardium, skin patches, blood vessels and ureters.

Preferred pre-treatment agents include fluorescein isothiocyanate (FITC) and picrylsulphonic acid (PSA) which react with the lysine residues of the collagen-based material. Other electrophilic chemicals could be used as the pre-treatment agent including alkyl and aryl acid halides, water stable anhydrides and esters, isothiocyanates and any other agent that combines with primary amine groups.

Nitrous acid or reagents involving the nitrite ion can also be used. It appears to act mainly by removing the amine group to produce nitrogen gas and a modified lysine side chain which does not react with the cross-linking agent.

A preferred cross-linking agent is glutaraldehyde which binds to the primary amines of the amine acid side chains of the collagen-based material, particularly the lysine residues. Other difunctional agents that can perform the same function include glyoxal, malonaldehyde, succinaldehyde, adipaldehyde, dialdehyde starch and adipyldichloride. Some monofunctional agents such as formaldehyde, acrolein and acetaldehyde can also be used.

The treatment conditions will, of course, vary according to the selection of the pre-treatment and cross-linking agents. For example, if the pre-treatment agent is FITC or PSA concentrations of 100 to 2000 milligram per litre could be used. If glutaraldehyde is the cross-linking agent concentrations of 0.2 to 5% could be used.

The temperature at which the pretreatment is carried out will, in the main, depend upon the selection of the pretreatment agent. Thus, the pretreatment temperature could be as low as $-15°$ C. and as high as $60°$ C. the period of pretreatment could vary from less than five minutes to more than 8 days.

The amount of collagen-based material treated in accordance with the process of the invention could vary from, say, 20 to 250 gram, per litre of pre-treatment agent.

The process of the invention is particularly suitable for the treatment of kangaroo tail tendons or bovine pericardium to minimize antigenicity but with minimal sacrifice of functional integrity.

The invention provides a human implantable collagen based material in which only some of the amino acid side chains are cross-linked.

DESCRIPTION OF PREFERRED EMBODIMENTS

In one example of the invention, a human implantable collagen-based material was prepared from kangaroo tail tendon. The skin of the kangaroo tail was first removed by carefully cutting away some of the skin with a scalpel without damaging the underlying tissue. The loosened skin was then grasped and the whole skin peeled. Throughout the dissection process the tissue was kept moist with sterile saline solution.

As most of the larger tendons lie immediately below the skin, they were exposed when the skin was removed. Each tendon was individually cut near its proximal attachment to muscle and its distal attachment to bone and then removed. It was immediately immersed in a tray of cold sterile saline solution. After soaking in this bath for one to two hours, the tendons were sorted to remove damaged material and loose tendon sheathing before being immersed in fresh cold saline solution.

The tendons were then subjected to chemical pretreatment with a reagent capable of reacting with the primary amines of the amino acid side chains of the collagen. The pre-treatment reagents used were fluorescein isothiocyanate and picrylsulphonic acid which were dissolved in a bicarbonate buffer at 750 and 500 mg/litre respectively. Approximately 500 ml of one of these solutions was used per 70 gm of tendon. The tendons were removed from the cold saline solution and placed in a container of the cold treatment reagent in which they remained for three days at approximately $4°$ C.

After the pre-treatment, the tendons were fixed in purified and buffered 2% glutaraldehyde for three days at room temperature. Each tendon was laid out lengthwise in a rack and lightly clamped at each end to minimize curvature. Each rack was immersed in a tray of the 2% glutarldehyde with 70 gm of tendon in approximately 700 ml of glutaraldehyde.

After the glutaraldehyde fixation step, each 70 gm of tendon was aseptically rinsed for at least seven minutes (including a minimum of two minutes of agitation) in a tray containing one litre of cold saline solution. This procedure was repeated twice more with fresh cold saline solution. The tendons were then aseptically transferred to their final packaging which was then filled with the final packaging solution prior to terminal sterilization by gamma radiation.

The Xenografts so prepared were expected to have applications in the treatment of sports injuries of the knee particularly in cruciate ligament repair. Furthermore, the Xenografts have potential as other ligament substitutes as well as for tendon repair or substitution.

In the case of the anterior cruciate ligament, one or more of the long tendon strands could be wound through tunnels drilled in the femur and tibia, so as to give a multi-stranded product that closely mimics the action of the cruciate ligaments of the knee.

In another example, a material suitable for hernia repair was prepared from bovine pericardium. Whole hearts with the pericardium intact were procured immediately after slaughter of the beast. The pericardium was carefully dissected from the heart as a single flat sheet and immediately immersed in a cold sterile saline solution. After soaking in the saline bath for one to two hours, the pericardium was cleaned to remove extraneous material and then immersed in a fresh cold saline solution.

The pericardium was then subjected to chemical pretreatment with nitrous acid. One suitable pretreatment solution is 6.9g of sodium nitrite dissolved on one litre of phosphate buffer. Each pericardium was placed in a dish with about 100 ml of the cold pretreatment solution and kept at approximately $4°$ C. for 24 hours.

After the pretreatment, the pericardium was rinsed in cold saline solution and fixed in purified and buffered 2% glutaraldehyde for 7 days at $4°$ C. Each pericardium was laid out flat in a dish in about 100 ml of the 2% glutaraldehyde.

After the glutaraldehyde fixation step, each pericardium was aseptically rinsed for at least 30 minutes in a tray containing about 500 ml of sterile saline solution. This procedure was repeated twice more with fresh sterile saline solution. Each pericardium was then aseptically transferred to the final packaging, filled with the final packaging solution and terminally sterilized by gamma radiation.

The pericardium material so prepared is expected to have applications in the treatment of hernias. For example it may be used as a reinforcing patch. The treated pericardium material also has other potential applications such as in the repair of pericardium or as a tendon sheathing material.

A further application of the invention could be the production of a repair/suturing material that has an intermediate life of, say, three to twelve months rather than either a few days as with rapidly dissolving sutures or many years as with very slowly degrading synthetic materials. Smaller diameter kangaroo tendons will provide an adequate intermediate life suturing material.

Various modifications may be made in details of the process and the product without departure from the scope and ambit of the invention.

We claim:

1. A process for preparing an implantable collagen-based material which comprises:
   (i) pretreating a collagen-based material with a member selected from the group consisting of fluorescein isothiocyanate, picrylsulphonic acid and nitrous acid, in an amount sufficient to render some of the amino acid side chains of the material unable to bind with a cross-linking agent, and
   (ii) reacting the pretreated collagen-based material with a cross-linking agent whereby at least some of the remaining amino acid side chains are linked together.

2. A process according to claim 1, wherein said pretreating is carried out with a member selected from the group consisting of fluorescein isothiocyanate or picrylsulphonic acid, at a concentration of 100 to 2000 milligrams per liter at a temperature of from $-15°$ C. to $60°$ C., and wherein the amount of collagen-based material ranges from 20 to 250 grams per liter of pretreatment agent.

3. A process according to claim 1 wherein the collagenous material is selected from the group comprising ligaments, tendons, heart valves, dura mater, pericardium skin patches, blood vessels and ureters.

4. A process according to claim 3 wherein the collagen-based material is selected from the animal source bovine, porcine, ovine, equine and kangaroo.

5. A process according to claim 1 wherein the cross-linking agent is selected from the group comprising glutaraldehyde, glyoxal, malonaldehyde, succinaldehyde, adipaldehyde, dialdehyde starch, adipyldichloride, formaldehyde, acrolein and acetaldehyde.

6. An implantable collagen-based material prepared in accordance with the process claimed in claim 9.

* * * * *